United States Patent [19]
Barton et al.

[11] Patent Number: 5,463,089
[45] Date of Patent: Oct. 31, 1995

[54] PREPARATION OF AMBROX

[75] Inventors: Derek H. R. Barton; Shyamal I. Parekh; Dennis K. Taylor; Chi-lam Tse, all of College Station, Tex.

[73] Assignee: Quest International B.V., Vlaardingen, Netherlands

[21] Appl. No.: 279,160

[22] Filed: Jul. 22, 1994

[51] Int. Cl.[6] .................................................. C07D 307/92
[52] U.S. Cl. ............................................................. 549/458
[58] Field of Search ................................................ 549/458

[56] References Cited

U.S. PATENT DOCUMENTS 4,872,917  10/1989  Howe et al. ............................. 113/275

OTHER PUBLICATIONS

Wahlberg et al., Acta Chemica Scandinavica B 31 pp. 453–459 (1977).

Barrero et al., Tetrahedron, vol. 49, pp. 10405 . 10412 (1993).

Bowles et al., Synlett, vol. 2, pp. 111–112 (1993).

*Primary Examiner*—Bernard Dentz
*Attorney, Agent, or Firm*—Cushman Darby & Cushman

[57]  ABSTRACT

Synthesis of (-)-dodecahydro-3a,6,6,9a-tetramethyl-naphtho(2,1-b)furan from sclareol in a three-stage process.

7 Claims, No Drawings

PREPARATION OF AMBROX

The present invention relates to the synthesis of the fragrance compound 1,2,3a,4,5,5a,6,7,8,9,9a,9b-dodecahydro-3a,6,6,9a-tetramethylnaphtho-(2,1-b)-furan which is also known as (-)-norlabdane oxide.

BACKGROUND OF THE INVENTION

Norlabdane oxide may be structurally shown as follows:

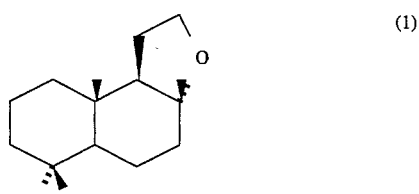

(1)

Compound (1) is presently one of the most commercially important perfume components for providing ambergris-type odors. Ambergris is a metabolic product of sperm whales which has been used in the past as a valuable constituent of fine fragrances.[1] Natural ambergris itself is no longer used for this purpose. However, there is a demand for perfume ingredients with ambergris-type odors. Compound (1) represents one of the preferred synthetic compounds with desirable ambergris-type odor and is commercially available under various names (notably as Amberlyn, Ambroxan, Ambrox or Amberoxide).[2]

Since the first reported synthesis of compound (1),[3] a number of synthesis procedures have been proposed. However, these are complex and laborious procedures which provide only a low yield of the desired product. Typically, these procedures include synthesis from sesqui- and diterpenoids.[4] More recently, it has been shown that naturally occurring (-)-sclareol[5,6] or communic acid[7,8] can be used as starting materials to prepare (1).

The reported procedures in going from the naturally occurring sclareol of structure (2):

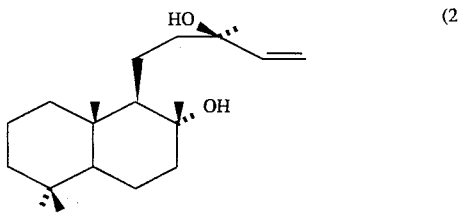

(2)

to the desired compound (1)[5,6], are, generally speaking, preferable to the communic acid pathways because the overall yields seem to be higher using (2), apparently due to a decrease in the number of steps required. In any case, all of the previously known methods using sclareol (2), as well as the current industrial process,[1] lead to the formation of the diol (3):

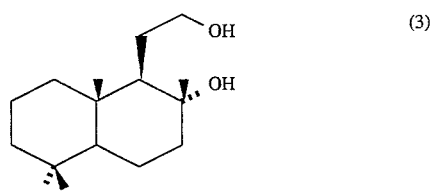

(3)

This must then be cyclized to give compound (1). This requires considerable care as the less desired, more thermodynamically stable iso-form of compound (1) may result[9,10]. This iso-form possesses inferior olfactive properties and serves to reduce the overall effectiveness of the synthesis process with respect to the production of compound (1).

In view of the foregoing, the principal object of the present invention is to provide a simplified but highly effective process for preparing compound (1) starting with sclareol. Other objects will also be hereinafter apparent.

SUMMARY OF THE INVENTION

Broadly described, the process of the invention involves a three-stage synthesis of compound (1) starting with sclareol (2) which avoids the cyclization step referred to above. The process is illustrated by the following reaction sequence wherein sclareol (2) is subjected to $OsO_4$ oxidation or catalyzed rearrangement to form methyl-ketone intermediates (4a) and (4b) after which intermediates 4(a) and 4(b) are converted by Baeyer-Villiger oxidation to give the acetates (5a) and (5b) which are both then converted to the desired compound (1). An advantage of the process is that mixtures of (4a) and (4b) may be used without separation since the products (5a) and (5b) obtained therefrom both give the desired compound (1) on reduction.

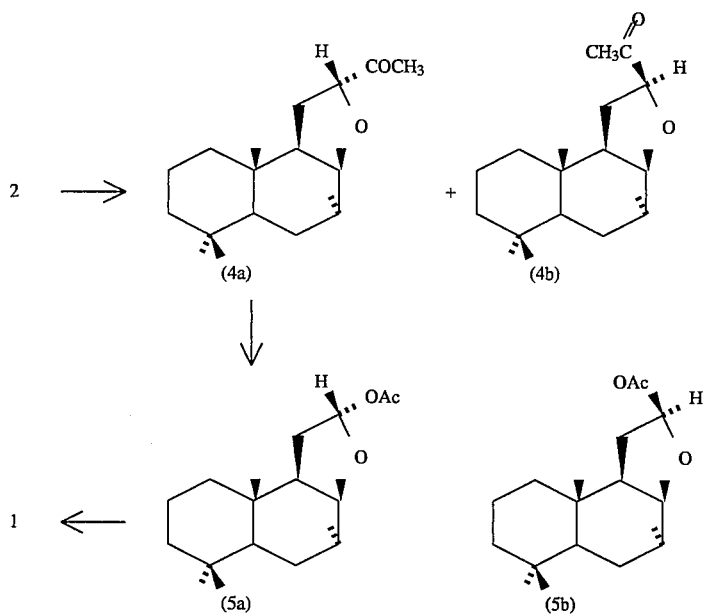

While the intermediate (4a) and (4b) are known (*Acta. Chem. Scand.*, B31, 1977, pages 453–459), the osmium tetroxide catalyzed rearrangement of sclareol to obtain these intermediates, under the conditions used herein, is believed to be novel. Step (2) of the process and the resultant acetates (5a) amd (5b), as well as the conversion of compounds (5a) and (5b) to (1), are also considered to be novel and constitute important features of the present invention.

PREFERRED EMBODIMENTS OF THE INVENTION

It will be appreciated that various modifications may be made in carrying out the above-described three-stage synthesis of compound (1) from sclareol (2). Thus, reaction conditions such as temperatures, solvents, reaction times, can be relatively widely varied without departing from the spirit and scope of the invention. Accordingly, the following procedure is given as representative of only one preferred way of practicing the invention:

Sclareol (2) may be reacted in a buffered alcohol (t-butanol) solution (pH≈1.0) of osmium tetroxide and sodium periodate at ambient temperature (20°–25° C.). After 5 hours, an epimeric mixture of the methyl ketones (4a) and (4b) is obtained in excellent yield, e.g., over 90% in a 9:1 ratio of (4a):(4b). The major epimer (4a), after separation from (4b) or preferably the mixture of (4a) and (4b), is then subjected to Baeyer-Villiger oxidation by adding m-CPBA and anhydrous sodium acetate to a solution of (4a), or in anhydrous dioxane to obtain, respectively, the acetate (5a) or mixture of (5a) and (5b). The resulting acetate or acetate mixture is obtained in high yield (e.g. about 90%) after which this product may be converted quantitatively to the desired compound (1), using $LiAlH_4$ in the presence of $BF_3.OET_2$ at low temperature (−78° C.).

As noted, separation of (4b) from (4a) is not necessary to effectively obtain the desired compound (1) since both (5a) and (5b) give (1) in high yield.

It will be appreciated that the above reaction conditions are only given as representative of a preferred way of practicing the invention. The essential features of the process as illustrated include the osmium tetroxide/periodate oxidative degradation or rearrangement of sclareol to the ketone (4a) or mixture thereof with (4b), oxidation of either 4(a) to the acetate (5a), or mixture of (4a) to (5a) and (5b), followed by conversion of the acetate or acetate mixture to compound (1).

The invention is further illustrated by the following examples:

Example 1

To sclareol (0.5 g, 1.62 mmol) dissolved in a t-butanol/water mixture (21 mL, 20:1) was added osmium tetroxide (5 mol %) and the mixture stirred at ambient temperature (20° C.) for 30 minutes. Sodium meta-periodate (0.35 g, 1.62 mmol) was added and the pH adjusted to 1.0 with phosphoric acid. Additional periodate was then added after 15 minutes (0.35 g, 1.62 mmol) and 45 minutes (0.52 g, 2.43 mmol) and the mixture stirred for an additional 5 hours. Column chromatography (hexane/ether 4:1) gave pure (4a), m.p. 71°–73° C., $[\alpha]_D$+44.43, c=1, $CHCl_3$. Anal. Calc. for $C_{18}H_{30}O_2$; C, 77.65; H, 10.85, Found: C, 78.04, H, 11.02.

The stereochemistry of the two epimers (4a) and (4b) was assigned on the basis that none of (4a) isomerized to (4b) on treatment with base. MOPAC6/PM3 optimization calculations on (4a) and (4b) showed (4a) to be 1.04 kcal/mol more thermodynamically stable than (4b).

To (4a) (1.0 g, 3.6 mmol) dissolved in anhydrous dioxane (20 mL) was added meta-chloroperbenzoic acid (m-CPBA, 0.72 g, 4.1 mmol) and anhydrous sodium acetate (0.65 g, 7.9 mmol). The mixture was stirred at ambient temperature for 24 hours after which time it was poured into saturated aqueous sodium bicarbonate solution (50 mL). The mixture was then extracted with dichloromethane (3×50 mL). The combined organic layers were then dried ($MgSO_4$ and the solvent removed in vacuo. Column chromatography (hexane/ether 4:1) gave pure (5a). However, it was noted that epimers (4a) and (4b) did not need to be separated and that, without such separation, the overall yield of (1) was increased.

Compound (5a) was characterized as follows: m.p. 92°–94° C., $[\alpha]_D$ –54.26, c=1.21, $CHCl_3$. Anal. Calc. for $C_{18}H_{30}O_3$; C, 73.42; H, 10.27. Found: C, 73.50, H, 10.33.

To an etheral solution (10 mL) of $LiAlH_4$ (0.07 g, 1.8 mmol) at 0° C. under argon was added borontrifluoride-etherate (0.75 mL, 6.7 mmol). Stirring of the mixture was continued for 30 minutes after which time the mixture was cooled to –78° C. and a solution of compound (5a) (0.5 g, 1.7 mmol) in anhydrous ether (5 mL) added. Stirring was continued for 30 minutes and the solution allowed to attain ambient temperature. After 3 hours, the mixture was poured into saturated aqueous bicarbonate solution (20 mL) and extracted with either (3×30 mL). Desiccation of the organic layers and removal of the solvent afforded (1). Column chromatography (hexane/ether 6:1) gave pure (1). Triethylsilane or the borane-THF complex and boron trifluoride-etherate could also be used for the reaction to give near-quantitative yields of compound (1).

Example 2

Step 1

To 0.5 g of pure sclareol, 0.02 of $OsO_4$ was added. Then 20 ml of distilled t-butanol and 1 ml of distilled water were added and the mixture was stirred at room temperature (20°–25° C.) for 30 minutes; by that time, a black solution resulted. To the black solution, 0.43 g of $NaIO_4$ was added, the solution was stirred and the pH was measured with a pH meter. The pH was around 2.5.

Phosphoric acid was added until pH=1. The solution was then allowed to stir for another 30 minutes.

0.45 g of $NaIO_4$ was added and, after stirring for another 30 minutes, 0.51 g of $NaIO_4$ was added. The solution now became an orange suspension and was continued to stir at room temperature.

The reaction was completed in 5 hours and was followed by TLC.

After the reaction was completed, the reaction mixture was poured into a solution of 5 g $Na_2S_2O_3.5H_2O$ in 100 ml of water. 50 ml of methylene chloride was added, extracted and the aqueous phase was extracted two more times with 50 ml methylene chloride, respectively. The organic layers combined and dried and the solvent evaporated.

After careful Column chromatography of the crude, 85% of (4a) and 9% of (4b) were isolated.

The foregoing may be modified in various ways. For example, other inorganic or organic acids such as sulphuric acid, sulphonic acid, $MeSO_2OH$, $CF_3COOH$ and the like can be used in place of phosphoric acid. Additionally, while ambient temperature is illustrated, the reaction temperature may be in the range of 0°–50° C. or even higher. The reaction time will also vary and will depend, at least to some extent, on the temperature used. Typical reaction times include 5–10 hours. It will also be appreciated that the TLC and Column chromatography used above may be replaced by equivalent separation techniques.

While the pH for the $OsO_4$ oxidation and the ratio of $OsO_4$ and periodate can be varied within limits, it has been noted, as discussed below, that the pH should not generally exceed 4 and the molar ratio can also be varied within limits, as noted hereafter. Normally, best results are obtained at a pH in the range of 0.5–2 and a molar ratio of periodate to $OsO_4$ of 2–4:1.

Step 2

As indicated earlier, compounds (4a) and (4b) do not need to be separated for this part of the overall synthesis. Accordingly, to 1 g of (4a)/(4b) mixture in a 50 ml round bottomed flask, 1.2 g of 6% m-CPBA (Aldrich) and 0.65 g of NaOAc were added. 20 ml of distilled dioxane was then added and the mixture was stirred at room temperature for 1 day. A milky suspension resulted.

The polarity of the starting material and the product are so close that TLC is not satisfactory in following the reaction. Accordingly, NMR was used to follow the reaction.

After stirring at room temperature for 1 day, the reaction mixture was poured into 50 ml of saturated aqueous sodium bicarbonate solution and diluted with 50 ml methylene chloride. After the extraction, the organic layer was separated, the aqueous layer was extracted with 3 more portions of 25 ml $CH_2Cl_2$, the organic layers were combined, dried and the solvent was evaporated.

To purify the resulting compound (5a), flash Column chromatography was used; gradient elution with hexanes and ether. Compound (5a) eluted out at around 15% ether in hexanes. A maximum yield of 75% of compound (5a) was obtained.

As in Step 1, modifications are possible in Step 2 as described in this example. For example, Caro's acid $H_2SO_5$, perphosphoric acid or urea hydroperoxide may be used as reactants with the (4a)/(4b) mixture. The reaction temperature can be varied from, for example, 0°–30° C. or higher and time in the order of 1–2 days or so may be used. The number of extractions is not critical and flash filtration, as an example, can be used in lieu of column chromatography.

Step 3

To 0.07 g of $LiAlH_4$ in 10 ml of ether at 0° C., 0.85 ml dry distilled $BF_3.Oet_2$ was added. The mixture was stirred for 30 minutes, then it was cooled to –78° C. with dry ice/acetone. A solution of 0.5 g of compound (5a) was then added and the mixture was stirred at –78° C. for 30 minutes. The temperature was then raised slowly to room temperature.

The reaction was completed in about 3 hours and was followed by TLC.

After the reaction was completed, the reaction mixture was poured slowly to saturated aqueous sodium bicarbonate solution and 50 ml ether was added. After the extraction, the aqueous layer was extracted with 3 more portions of 25 ml ether, the organic layer was combined, dried and solvent was removed. The crude contained almost pure compound (1).

Compound (1) was purified by column chromatography to give a yield of 100% based on (5a).

While (5a) was separated in step 2 for conversion to (1), this was found not to be necessary since (5b) is likewise converted to compound (1) using step (3) to obtain an even higher overall yield.

It is noted that Barrero et al[6] have described the $OsO_4$/$NaIO_4$ oxidation of sclareol (2) as the first step in their synthesis. However, their oxidative cleavage of (2), which was carried out in THF at 45° C., afforded an aldehyde, identified as compound (6) in Scheme 2 below as the major product along with a number of other minor products, one of which was (4a) (2%). The difference in Barrero's results and the present process is not apparently due to such reaction conditions as solvent or temperature variations. It is believed that the formation of (4a) and (4b) and/or (6) is strongly dependent on the periodate/$OsO_4$ ratio. This is more clearly seen by considering the mechanism for the formation of (4a) and (4b) or (6) in Scheme 2.

Scheme 2

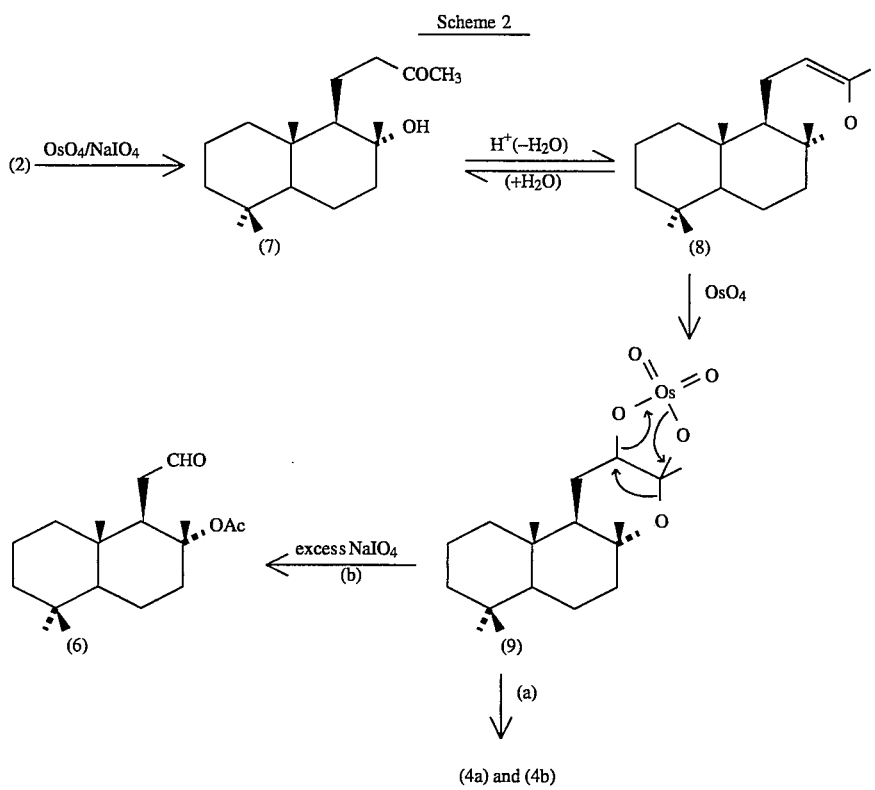

While not wishing to be bound to any particular theory, it is thought that oxidative cleavage of (2) affords the uncyclized methyl-ketone (7) which under acidic conditions cyclizes to enol-ether (8). Osmylation of the double bond in (8) gives the intermediate (9). It is believed that because the mole ratio of $NaIO_4/OsO_4$ used herein is lower than that for Barrero's, intermediate (9) has time to rearrange in the present process to the observed epimeric methyl-ketones (4a) and (4b). However, if the $NaIO_4/OsO_4$ ratio is high, e.g. above 4, then cleavage to the aldehyde (6) is favored over rearrangement. A repeat of Example 2 but using 1% $OsO_4$ and 6 equivalents of $NaIO_4$ (mole ratio, 600) shows aldehyde (6) to be the major product (62%) along with the methyl-ketone (4a), 10%.

The relative proportions of (4a), (4b) and (6) have also been found to vary with pH. For example, buffering the mixture to pH<4 with $H_3PO_4$, gave only (4a) and (4b) while using the pH range (4.6–7.2) the undesired aldehyde (6) was produced in 14% yield along with (4a) and (4b).

As will be evident, the process of the invention provides a relatively straightforward, three-step synthesis for preparing compound (1) starting with sclareol. The synthesis is a simple one which gives compound (1) in high yield (e.g. in the order of 70–75% overall). A key step of the process is the osmium catalyzed rearrangement step which, as noted above, is dependent, for best results, on the use of an acid pH of up to about pH 4 and a molar ratio of periodate/$OsO_4$ not in excess of 4.

The following publications are referred to earlier herein:

REFERENCES

1. Sell, C., *Chemisty and Industry*, 20:516–520, 1990
2. Ohloff, G., *Fragrance Chemistry. The Science of the Sense of Smell*, Theimer, E. T.; Academic press, New York, 1982, pp. 535–573
3. Stoll, M., Hinder, M., *Helv. Chim. Acta*, 33:1251–1261, 1950;Hinder, M., Stall, M., *ibid* 1308–1312
4. Gonzalez-Sierra, M., Ruvida, E. A., Lopez, J. T., Cortes, M. J., *Hetercycles*, 26:2801–2804, 1987; Schenk, H. R., Gutman, H., Jeger, O., Ruzicka, L., *Helv Chim. Acta*, 37:543–546, 1954; Cambie, R. C., Joblin, K. N., Preston, A. F., *Aust. J. Chem.*, 24:583–591, 1971; De-Pascual, T. J., Urones, J. G., Montana, P. A., Basabe, P., *Tetrahedron Lett.*, 26:5717–5720, 1985; Koyama, H., Kaka, Y., Ohno, M., *Tetrahedron Lett.*, 28:2863–2866, 1987; Nishi, Y., Ishihara, H., *J. Jpn. Oil Chem. Soc.*, 38:26–279, 1989
5. Martres, P., Perfetti, P., Zahra, J. P., Waegell, B., Giraudi, E., Petrzilka, M., *Tetrahedron Lett.*, 34:629–632, 1993; Martres, P., Perfetti, P., Zahra, J. P., Waegell, B., *Tetrahedron Lett.*, 32:765–766, 1991; Coste-Maniere, I. C., Zahra, J. P., Waegell, B., *Tetrahedron Lett.*, 29:1017–1020, 1988; Martres, P., Perfetti, P., Zahra, J. P., Waegell, B., *Tetrahedron Lett.*, 35:97–98, 1994
6. Barrero, A. F., Enrique, J. E., Manzaneda, A., Altarejos, J., Salido, S., Ramos, J. M., *Tetrahedron*, 49:10405–10412, 1993
7. Barrero, A. F., Altarejos, J., Enrique, J. E., Manzaneda, A., Ramos, J. M., Salido, S., *Tetrahedron*, 49:6251–6262, 1993
8. Barrero, A. F., Altarejos, J., Enrique, J. E., Manzaneda, A., Ramos, J. M., Salido, S., *Tetrahedron*, 49:9525–9534, 1993
9. Buchi, G. Wuest, H., *Helv. Chim. Acta*, 72:996–999, 1989

10. Decorzant, R., Vial, C., Naf, F., *Tetrahedron*, 43:1871–1879, 1987

Various modifications may be in the invention as described above. For example, the $OsO_4/NaIO_4$ system used in Step 1 may be replaced by $OsO_4/H_5IO_6$ or other equivalent $OsO_4$/periodate system. The scope of the invention is, therefore, defined by the following claims wherein:

We claim:

1. A process for preparing (-)-dodecahydro-3a,6,6,9a-tetramethylnaphtho(2,1-b)furan of the formula (1):

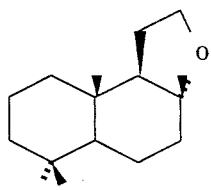
(1)

which comprises:

(i) converting sclareol of the formula (2)

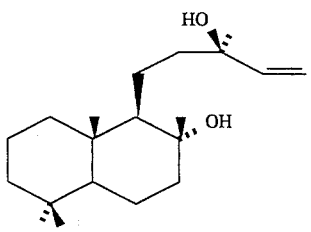
(2)

to methyl ketones of the formulae:

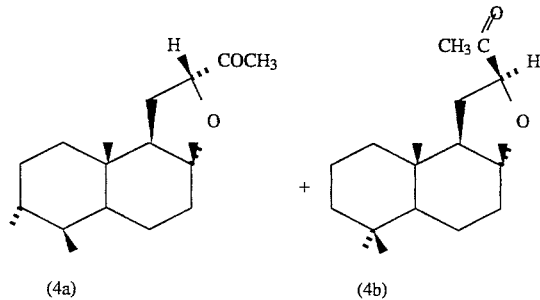
(4a)      (4b)

(ii) converting said ketone (4a) or mixture thereof with (4b) to, respectively, an acetate of the formula (5a) or mixture of acetates (5a) and (5b):

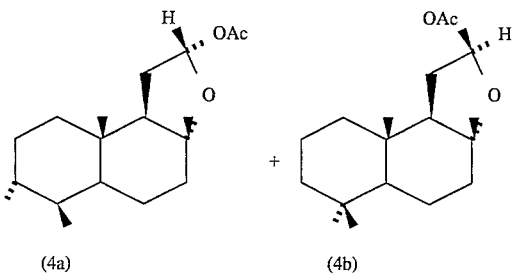
(4a)      (4b)

and (iii) converting said acetate (5a) or acetate mixture (5a) and (5b) to said compound (1).

2. The process of claim 1 wherein the conversion in step (i) is carried out at a pH of 4 or less using a $OsO_4$/periodate catalyst.

3. The process of claim 2 wherein the catalyst is $OsO_4NaIO_4$ and the mole ratio of $NaIO_4$ to $OsO_4$ is less than 4.

4. The process of claim 3 wherein step (ii) comprises oxidation of (4a) or mixture of (4a) and (4b).

5. The process of claim 4 wherein the oxidation of 4(a) and 4(b) is a Baeyer-Villiger oxidation.

6. The process according to claim 1 wherein step (iii) is carried out by deacetoxylation of compound (5a) and 5(b).

7. A compound selected from the group consisting of compounds of the formulae (5a) and (5b):

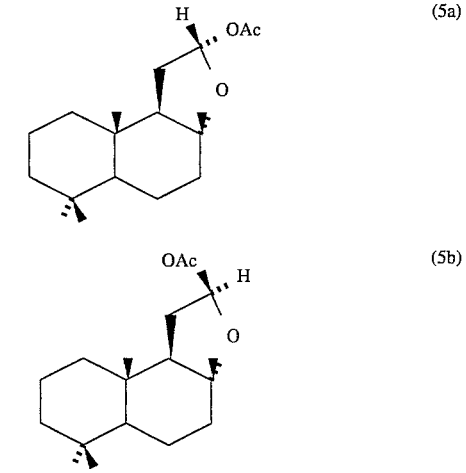
(5a)

(5b)

* * * * *